United States Patent [19]

Joines et al.

[11] Patent Number: 4,817,635
[45] Date of Patent: Apr. 4, 1989

[54] INTERSTITIAL APPLICATOR WITH CANCELLATION/ENHANCEMENT GAP

[75] Inventors: William T. Joines; Yang Zhang, both of Durham; James R. Oleson, Chapel Hill, all of N.C.

[73] Assignee: Duke University, Durham, N.C.

[21] Appl. No.: 29,119

[22] Filed: Mar. 23, 1987

[51] Int. Cl.$^4$ .............................................. A61N 5/02
[52] U.S. Cl. .............................. 128/804; 219/10.55 F
[58] Field of Search ............... 128/804, 784, 786, 401; 219/10.55 R, 10.55 F

[56] References Cited

U.S. PATENT DOCUMENTS

| | | | |
|---|---|---|---|
| 3,230,957 | 1/1966 | Seifert | 128/804 |
| 4,612,940 | 9/1986 | Kasevich et al. | 128/804 |
| 4,700,716 | 10/1987 | Kasevich et al. | 128/804 |

FOREIGN PATENT DOCUMENTS

| | | | |
|---|---|---|---|
| 0105677 | 4/1984 | European Pat. Off. | 128/804 |
| 1188490 | 4/1970 | United Kingdom | 128/804 |

Primary Examiner—Lee S. Cohen
Attorney, Agent, or Firm—Oblon, Fisher, Spivak, McClelland & Maier

[57] ABSTRACT

An interstitial applicator is provided in order to heat a localized region of living tissue by simultaneously enhancing energy passed at the end of a central conductor while cancelling signals traveling along the outside of the application by forming a gap in the outer conductor of a coaxial cable with the gap being located ¼ wavelength from the end of the outer conductor. The width of the gap corresponds to ⅛ of the diameter of the coaxial cable which forms the applicator. This system provides for an enhancement of the heating at the particular area around the tip of the central conductor while at the same time forms a block to stop surface wave heat from travelling back to the skin/tissue surface.

6 Claims, 3 Drawing Sheets

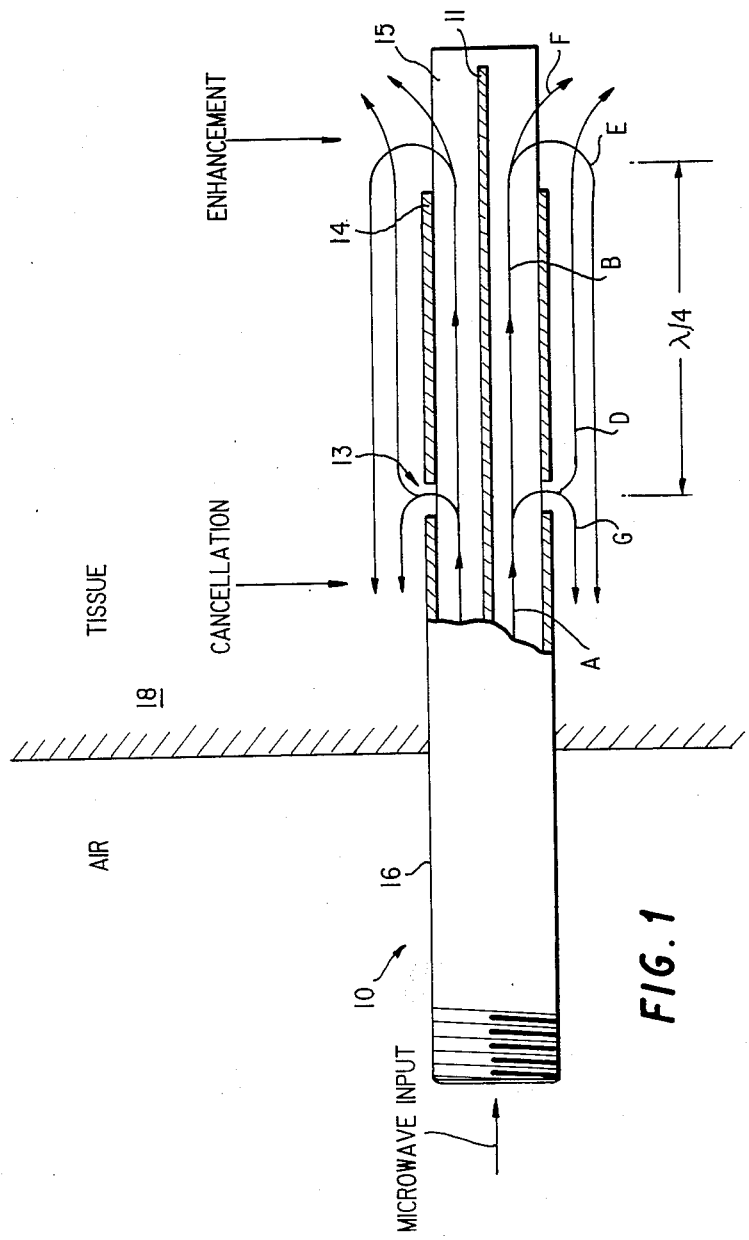

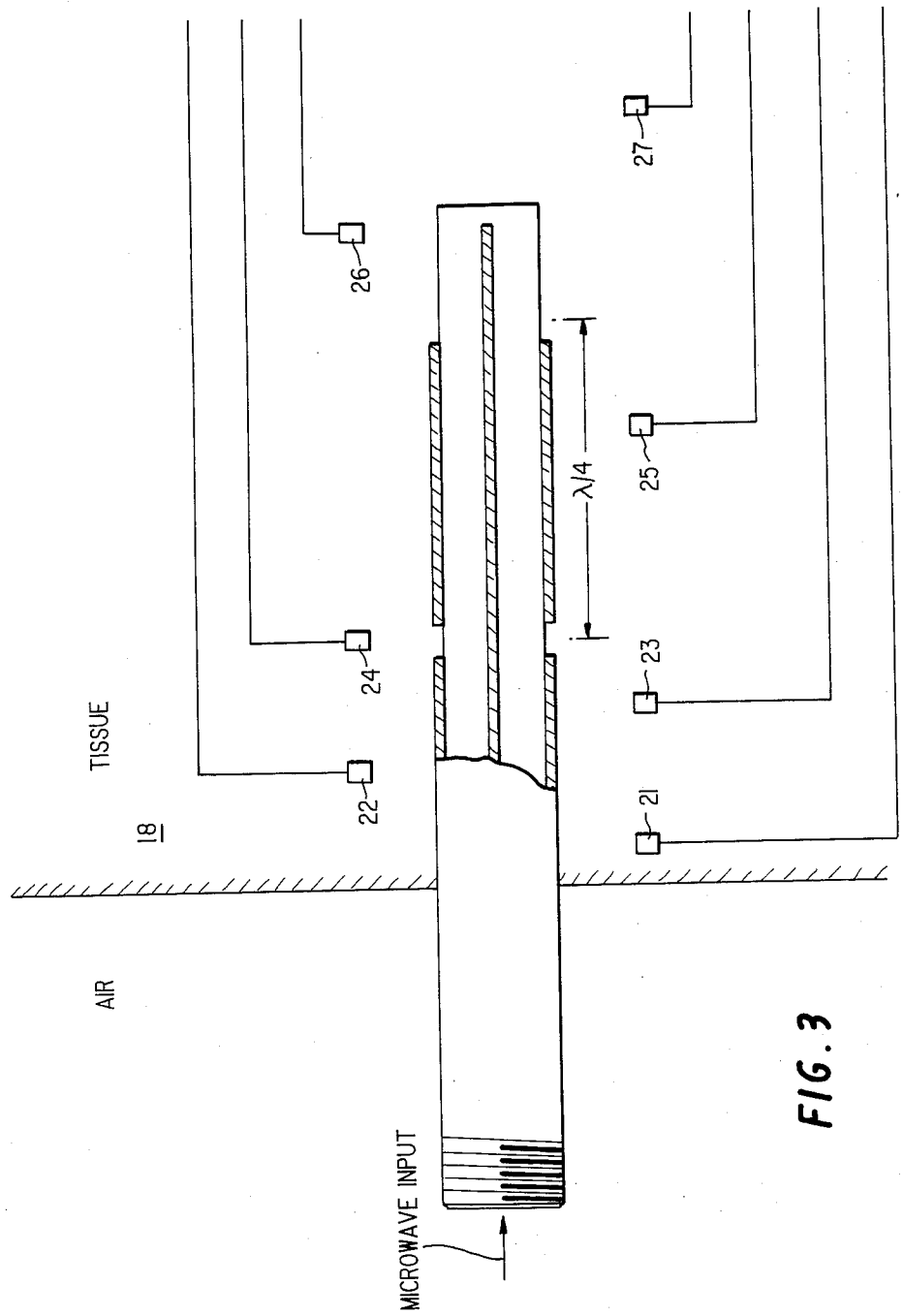

INTERSTITIAL APPLICATOR WITH CANCELLATION/ENHANCEMENT GAP

BACKGROUND OF THE INVENTION

1. Field of the Invention

The present invention relates to an improved interstitial heat applicator whereby a local area of human or animal living tissue is heated by electromagnetic radiation.

2. Discussion of Background

Prior art microwave interstitial applicators utilize a conductor with a gap in the outer conductor. These type of structures invariably experience difficulty with respect to the energy which is radiated from the gap in the outer conductor of the applicator. Primarily, the difficulty is the travelling of the energy back along the surface of the outer conductor toward the input at the air-tissue interface. When this type of energy, which is radiated back along the outer conductor, is experienced, a heating pattern is developed so that heating occurs at the insertion point of the applicator. This is usually an undesirable result which in the very least detracts from the applicator's effectiveness and which creates not only a loss of heat at the point at which it is desired to be used but also provides an unintended heat "spot" where such heat spot is either uncomfortable or harmful. The harmful effects become more pronounced as higher power levels are used in order to heat localized growths by using a single applicator.

One type of prior art solution to this problem is disclosed in U.S. Pat. No. 4,448,198 wherein the applicators are provided with a "interconnecting means" in such a configuration so as to cause constructive interference within the emitted electromagnetic radiation when the applicators are inserted into the body tissue in a preselected spaced apart relationship. In a particular embodiment a plurality of parallel spaced applicators are placed in conjunction with an interconnecting means including a line stretcher to vary the phase of the electromagnetic energy provided to each applicator. Additionally, a catheter and a hypodermic needle are provided for inserting and positioning each applicator into the body tissue in a spaced apart relationship.

This and other prior art attempts to deal with these type of invasive hypothermia situations fail to provide accurate control of the applied power. That is, although the pattern of energy radiated from the gap and the outer conductor has been modified in the prior art with respect to its backward travel to the surface of the air-tissue interface, such modification is adapted to the particular situation and requires extensive modification for a different environment. Furthermore, the control of the spotting of the maximum heat is not at all precise and is not able to be duplicated from one application to another because of changing conditions and orientation.

SUMMARY OF THE INVENTION

It is an object of the present invention to provide a coaxial interstitial applicator which provides for enhancement of a desired radiation pattern at a specific location which at the same time provides for cancellation of undesired surface waves.

In accordance with a further object of the present invention, a gap, located a specific distance from the end of a probe and having a specific gap width, provides the particular enhancement of surface waves at the desired point of application and further the location and the size of the gap provides for the cancellation of surface waves to prevent unintended heating points or distorted heating patterns.

BRIEF DESCRIPTION OF THE DRAWINGS

A more complete application of the invention and many of the attendant advantages thereof will be readily obtained as the same becomes better understood by reference to the following detailed description when considered in connection with the accompanying drawings, wherein:

FIG. 1 is a cross-sectional view of a coaxial interstitial probe according to the present invention;

FIG. 3 shows a test arrangement utilized to provide the temperature results of FIG. 2A.

DESCRIPTION OF THE PREFERRED EMBODIMENTS

Figure 2A:
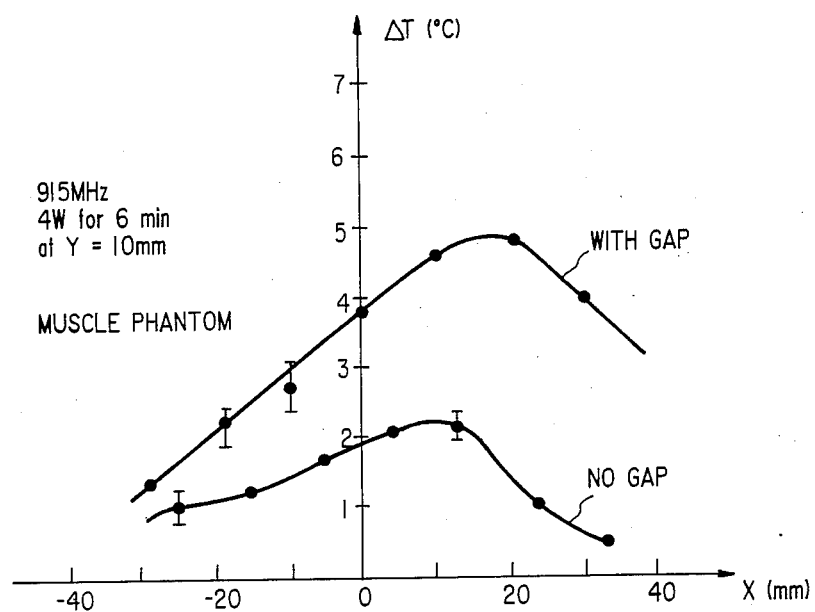
FIG. 2A is a graph of the heating patterns generated by the applicators of FIG. 2B and FIG. 2C respectively.

Referring now to the drawings, wherein like reference numerals designate identical or corresponding parts throughout the several views, and more particularly to FIG. 1 thereof, there is shown the coaxial interstitial probe of the present invention, in cross-section, inserted into the tissue. The input is a microwave energy source which is, for purposes of the primary embodiment, a source producing 915 MHz. The applicator 10 having the central conductor 11, is positioned substantially beneath the air-tissue surface. The thin, coaxial-line center conductor antenna 11 is inserted into the tumor without the need for protruding past the tumor into normal tissue, as was required in prior art type of applicators. The microwave energy which travels back up the outer conductor 12 toward the air-tissue interface is minimized by the later-discussed relationship between the end of the tip 11 and the location and width of the gap 13. This improves over prior art types of devices wherein the tip needed to be inserted past the tumor and the backward heating of the normal tissue at the air-tissue interface was a significant problem or at least an uncontrolled problem.

The embodiment of FIG. 1 contains a gap 13 in the outer conductor 14. The distance between the gap and the end of the outer conductor 14 nearest to the tip 11 is equal to ¼ wavelength ($\lambda/4$) wherein $\lambda$ represents the wavelength of the frequency resulting from the 915 MHz input and the dielectric constant which is equivalently, formed by the combination of the Teflon (polytetrafluoroethylene) dielectric 15 between the inner conductor 11 and the outer conductor 14 as well as the dielectric constant of a covering 16 and the equivalent dielectric constant of the tissue into which the applicator 10 is inserted. It must be noted that whereas the dielectric constant is the same for all frequencies with respect to the inner and outer copper conductors 11 and 14 and the TEFLON dielectric 15 as well as the covering 16, the dielectric constant for different frequencies changes with respect to the tissue 18. In other words the tissue has a permittivity which effectively produces a variation in the dielectric constant of the muscle tissue depending upon the different frequencies being applied to the microwave input.

The gap 13 functions most effectively when it is equal to ⅓ of the diameter of the coaxial probe 10. This is an experimental finding which will be developed in conjunction with the showings of FIG. 2.

The utilization of a ¼ wavelength for the distance between the gap 13 and the end of the outer conductor 14 provides for an enhancement near the end of the conductor 11 of any surface waves and further provides for a cancellation of surface waves at the gap 13. In order to see this more clearly, FIG. 1 shows an incoming wave A being divided into wave B which is passed down the probe and the waves C and D which are respectively passed through the gap 13 in both directions along the surface of the conductor 14 or the covering 16. At the end of the center conductor 11 the wave B is divided into return surface wave E and the wave F. Because the distance of travel of wave B is ¼ wavelength and because the return distance is another ¼ wavelength until the wave E reaches the gap 13 there has been a total of a ½ wavelength traversed by the wave E at the time it returns to the gap 13. This ½ wavelength provides for a 180° phase opposition to the wave C and therefore the wave E serves to cancel the contribution of wave C in order to eliminate any waves being passed to the air-tissue surface and thereby eliminating any uneven heating of the surface. Because of the aforementioned enhancement provided by wave D and wave F the portion near the tip 11 has increased heating.

Figure 2B:
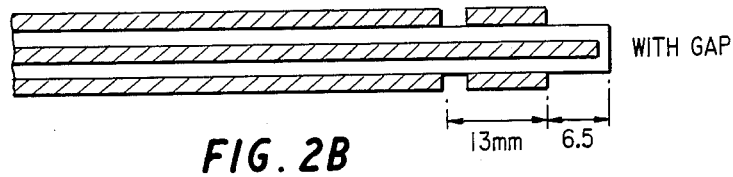
FIG. 2B illustrates an applicator with a gap according to the present invention which is utilized in the generating of the temperature graph of FIG. 2A.

The above discussed theoretical feature with respect to the ¼ wavelength and the subsequent cancellation at the ½ wavelength as well as the enhancement near the tip 11 is exemplified by the FIG. 2A which shows detailed measurements both with the gap and without the gap. The graph of FIG. 2A was obtained by utilizing an interstitial applicator having 915 MHz signal applied at a power of 4 watts for a time of 6 minutes. Measurements taken with respect to the temperature of tissue were taken with 7 temperature probes 21–27 (BSD 200 thermometry) which were inserted around the applicator (probe) in muscle equivalent tissue at a distance of 10 mm from the outer conductor 14 in such a manner as to surround the applicator as shown in FIG. 3.

The FIG. 2A shows the results as having a peak in temperature change at approximately 20 mm which, as shown in FIG. 2A, corresponds approximately to the tip of the applicator taking into account that for the particular embodiment, the distance between the gap and the end of the outer conductor was 13 mm with an additional 6.5 mm being utilized between the end of the outer conductor and the end of the center conductor 11. This clearly shows that the heat is most effectively conducted toward the end of the center conductor 11 which provides an even application of maximum heat in the particular region of interest. That is, if a tumor is located a specific distance from the skin surface, the device may be positioned so that the tip of the center conductor 11 is located precisely within the tumor itself. This is a vast improvement over the hit and miss situation with respect to the prior art and it is quite easy to position the tip within the tissue to be heated in contrast with attempting to pass the probe through the tissue to be heated until it is in vicinity of the gap, which was necessary with prior art type of devices.

Figure 2C:
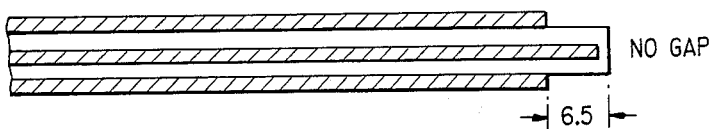
FIG. 2C represents an applicator without a gap used in the comparison graph of FIG. 2A.

It is to be noted that the development of the embodiments of FIGS. 2–3 is such that the structure will function in a similar manner for different applications to different tissues in different locations in the body. Any change however in the frequency applied calls for an adjustment in the distance which is equal to ¼ wavelength because, of course, the wavelength will vary not only because of the change in the applied frequency of the input power but also because of the aforementioned permittivity change in the muscle tissue. Therefore, a simple multiplication factor of ½ would not be effective if the frequency were doubled, for instance. This failure to provide a linear relationship is due to the aforementioned permittivity of the tissue and the fact that the equivalent dielectric constant is made up of each of the aforementioned items including the teflon dielectric between the inner 11 and outer 14 conductor and the covering 16, which is usually teflon.

Because of the complexity in calculating the effective wavelength due to the equivalent dielectric constant, which changes with the frequency on account of the permittivity of the muscle tissue, the maximum temperature change, for any other frequency may be determined experimentally by adjusting the distance between the gap and the end of the outer conductor 14 so that a maximum temperature change occurs at the approximate end of the center conductor 11 (tip). The 915 MHz frequency has been utilized because it is a normally accepted standard frequency application which has been approved by the FCC as one of the standard frequencies in medical applications.

The FIG. 2A further shows the positioning of the measuring points for each of the temperature probes shown in FIG. 3. The distances shown in FIGS. 2B and C are specific measurements which are utilized in the temperature measurements of FIG. 2A. The curve obtained for the gap as shown in FIG. 2A provided the maximum temperature change at the location of the tip. This maximum temperature curve was obtained when the gap 13 was limited to a value of ⅓ of the diameter of the cable. This ⅓ factor is an experimentally determined result and any change in applied frequency or change in diameter of cable used does not alter the effectiveness provided by keeping the ratio between the diameter of the cable and the length of the gap to a value of 3.

A change in the distance between the end of the tip of the inner conductor 11 and the end of the outer conductor 14 modified or shifted the curve of FIG. 2A and was thus undesirable because of either a lower temperature or a temperature peak which was not in the vicinity of the tip 11.

Although the maximum temperatures reached will be different, if different wattages and time frames and distances of the temperature probes from the coaxial cable are utilized, the basic curve structure of FIGURE 2A will remain the same and therefore any change in the applied wattage or the length of the time that it is applied or the distance from the particular probe will not effect the distances used for the length between the gap and the end of the outer conductor or the distance between the outer conductor and the tip of the inner conductor 11. As previously mentioned, a change in the application frequency of the input power will result in a requirement for the adjustment of the distance between the gap and the end of the outer conductor 14. This change in location of the gap, because of the change in frequency, is necessary in order to obtain an effective ¼ wavelength distance and this change is complicated by the fact that the dielectric constant or the equivalent dielectric constant of the material is not strictly proportional to any change in frequency because of the permittivity of muscle tissue. Thus a new frequency being applied requires an adjustment of the length which is equivalent to the ¼ wavelength and such adjustment can either be made through a series of calculations of the equivalent dielectric constant presented to the power input or by a experimental changing in the length in order to determine the most effective curve in order to obtain maximum temperature change at the tip of the conductor 11.

As previously mentioned the use of an effective ¼ wavelength distance between the gap and the end of the outer conductor 14 in combination with the utilization of a gap having a width equal to ⅛ of the diameter of the coaxial cable provides a system whereby backward traveling surface waves are cancelled and forward traveling waves are enhanced due to the phase relationship between the location of the gap in the outer conductor and the radiating end of the applicator. With this type of system there is no requirement for an insertion beyond the tumor volume because the heating patterns are shifted toward the tip of the applicator.

Experiments have shown that when four applicators of the type shown in FIG. 1 are arranged in a rectangular and a co-planar phased array, the pattern which is produced is a spherical heating pattern which is ideally suited for localized heating of tumors.

Obviously, numerous modifications and variations of the present invention such as implementation at different wavelengths are possible in light of the above teachings. It is therefore to be understood that within the scope of the appended claims, the invention may be practiced otherwise than as specifically described herein.

What is claimed as new and desired to be secured by Letters Patent of the United States is:

1. An interstitial applicator for heating a localized region of living tissue comprising:
   a coaxial means for transmitting electrical energy, said coaxial means having an inner conductor, an outer conductor surrounding coaxially said inner conductor and a dielectric separator positioned between said inner and outer conductor, a source of electromagnetic energy connected to one end of said coaxial means including one end of said inner and said outer conductor wherein said coaxial means further includes a gap formed in said outer conductor, said gap having a width substantially equal to ⅛ of the diameter of said coaxial means and wherein the distance between said gap and the other end of said outer conductor is substantially equal to ¼ of the effective wavelength of said electromagnetic energy wherein said effective wavelength is defined as the wavelength of the electromagnetic energy of said source modified by the effective dielectric constant formed by the combination of said dielectric between said inner and outer conductor and by said outer conductor and the environment in which said gap and said outer conductor are positioned.

2. An applicator according to claim 1, wherein said source of the electromagnetic energy includes a means for producing a signal of 915 MHz and wherein said distance between said gap and said other end of said outer conductor equals 13 mm.

3. The applicator according to claim 2, wherein said inner conductor extends beyond said outer conductor at said other end by approximately 6.5 mm.

4. The applicator according to claim 1, further comprising a thin covering placed over the outer conductor.

5. An interstitial applicator for heating a localized region of living tissue comprising:
   means for providing electromagnetic energy;
   means for receiving said electromagnetic energy and transmitting said energy into said living tissue wherein said means for receiving said electrical energy includes a central conductor having one end adapted to be positioned in said localized region to be heated;
   means responsive to said energy for outputting a first portion of said energy wherein said first portion is in phase opposition to a second portion of said energy wherein said second portion travels along the outside of said means for receiving away from said one end of said central conductor to thereby eliminate any heating due to electromagnetic energy travelling outside of said means for receiving.

6. The applicator according to claim 5, wherein said means for outputting a first portion includes a spaced apart section and wherein said spaced apart section allows for concentration of energy from said source at an area coinciding with said localized region.

* * * * *

UNITED STATES PATENT AND TRADEMARK OFFICE
CERTIFICATE OF CORRECTION

PATENT NO. : 4,817,635
DATED : April 4, 1989
INVENTOR(S) : William T. Joines ET AL It is certified that error appears in the above-identified patent and that said Letters Patent is hereby corrected as shown below:

In the Abstract: line 5, delete "application" and insert therefor --applicator--.

In the Abstract: line 12, delete "wave heat" and insert therefor --waves--.

In column 1: line 17, delete "travelling" and insert therefor --traveling--.

In column 1: line 46, delete "hypothermia" and insert therefor --hyperthermia--.

In column 4: line 31, delete "28" and insert therefor --2B--.

In Figure 1: delete "G" and insert therefor --C--.

In Figure 1: identify outer conductor by the number 12.

Signed and Sealed this

Second Day of January, 1990

Attest:

JEFFREY M. SAMUELS

Attesting Officer     Acting Commissioner of Patents and Trademarks